United States Patent [19]

Vaughan

[11] 4,316,997

[45] Feb. 23, 1982

[54] ALKYLATION PROCESS AND APPARATUS USEFUL THEREIN

[75] Inventor: Ronald J. Vaughan, Orinda, Calif.

[73] Assignee: Varen Technology, Marshallton, Del.

[21] Appl. No.: 64,480

[22] Filed: Aug. 7, 1979

Related U.S. Application Data

[63] Continuation-in-part of Ser. No. 660,634, Feb. 23, 1976.

[51] Int. Cl.$^3$ .............................. C07C 2/66; C07C 2/70
[52] U.S. Cl. ...................................... 385/458; 568/607
[58] Field of Search ........................................ 585/458

[56] References Cited

U.S. PATENT DOCUMENTS

| | | | |
|---|---|---|---|
| 3,708,553 | 1/1973 | Olah | 585/458 |
| 3,882,093 | 5/1975 | Cavanaugh et al. | 260/79.3 |
| 3,976,704 | 8/1976 | Vaughan | 260/645 |
| 4,041,090 | 8/1977 | McClure | 585/458 |

FOREIGN PATENT DOCUMENTS 895178  5/1962  United Kingdom .

OTHER PUBLICATIONS

Kapura et al., "Sulfonated Polymers as Alkylation Catalysts", Industrial Engineer Chemistry Product Research Development, vol. 12, No. 1, pp. 62–66 (1973).
Grot et al., paper "Perfluorinated Ion Exchange Membranes", presented at 141st Electrochemical Society Mtg., Houston, Tex., May 1972.

*Primary Examiner*—Curtis R. Davis
*Attorney, Agent, or Firm*—Charles J. Tonkin

[57] ABSTRACT

This invention relates to conversion processes which take place in the presence of solid acid catalysts, e.g., hydrocarbon conversion processes. More specifically, this invention relates to a liquid phase process for the alkylation of aromatic hydrocarbons, with olefin, e.g., ethylene, propylene, etc., in the presence of a polyfluorosulfonic acid catalyst.

7 Claims, 1 Drawing Figure

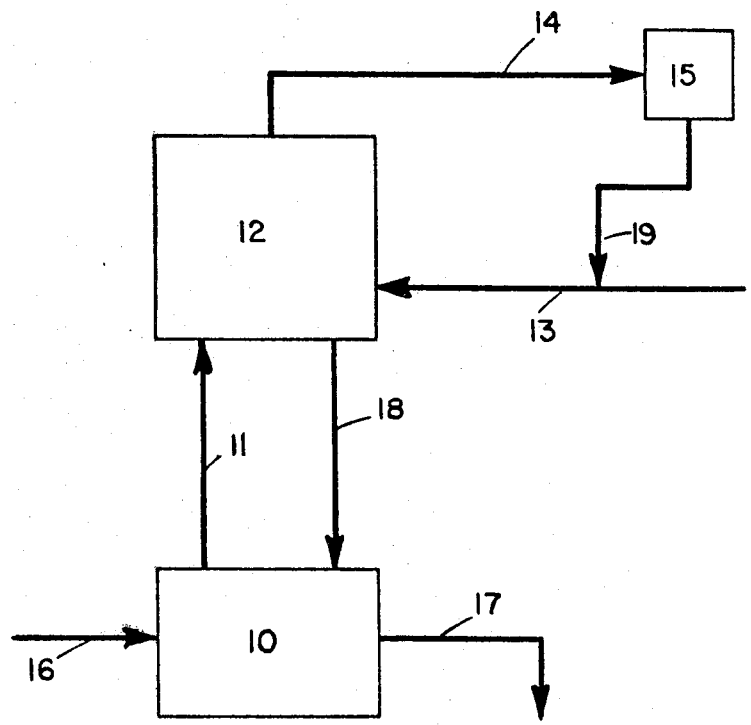

ALKYLATION PROCESS AND APPARATUS USEFUL THEREIN

This patent application is a continuation-in-part of U.S. Ser. No. 660,634, filed Feb. 23, 1976.

FIELD OF THE INVENTION

This invention relates to conversion processes which take place in the presence of solid acid catalysts, e.g., hydrocarbon conversion processes. More specifically, this invention relates to a process for the alkylation of aromatic hydrocarbons with olefins, e.g., ethylene, propylene, etc. in the presence of a polyfluorosulfonic acid catalyst. Preferably said organic compound is benzene and said olefin is selected from the group consisting of ethylene and propylene; especially preferred is the alkylation of benzene with ethylene at the higher temperatures.

BACKGROUND OF THE INVENTION

Alkylation refers generally to the addition of an alkyl group to an organic compound. One well-known alkylating agent useful in the preparation of a wide variety of alkylated derivatives is the olefin. For example, dodecylbenzene, a useful precursor for the surfactant industry may be prepared by the alkylation of benzene with dodecene in the presence of an aluminum chloride catalyst. The aluminum chloride catalyst continuously deactivates and forms a sludge which is recovered and regenerated only at great cost and difficulty. In all of these processes a solid catalyst which is easily separated from the reaction mixture is desirable.

Other examples of commercially important alkylation processes include the alkylation of benzene with ethylene to yield ethylbenzene, which may be subsequently converted to styrene; and the alkylation of benzene with propylene to yield cumene, which may be subsequently converted to phenol and acetone, respectively. Catalysts useful in these processes include phosphoric acid supported on kieselguhr and aluminum chloride. In each of the above benzene alkylation processes the tendency to form polyalkylated derivatives, as impurities, is a noted problem.

In U.S. Pat. Nos. 3,037,052; 3,107,441; and 3,239,575, the use of various forms of sulfonated polystyrene as a catalyst for alkylation processes is disclosed. The difficulties of using sulfonated polystyrene include (1) cleaning residual organic "tars" from the catalyst; (2) gradual changes in the catalyst properties due to the alkylation of unsulfonated styrene residues; and (3) physical fragility of highly sulfonated styrene-divinyl benzene copolymers. In these patents, there is no mention of the use of polyfluorosulfonic acid polymers as catalysts for the alkylation processes described herein. Thus, in U.S. Pat. No. 3,239,575 it is proposed to alkylate aromatic hydrocarbons using as a catalyst a sulfonated synthetic resin copolymer of a vinyl aromatic compound and a divinyl cross-linking agent, having less than 4 wt. % cross-linking, it being said that such resins having more than 4% cross-linking, as in conventional sulfonated polystyrene resins, have no activity for alkylation of benzene with polylene. However, such lower cross-linked polymers have disadvantageous properties of compressability, poorer strength, etc. In contrast, my fluorocarbon polymer sulfonic acids do not have these problems.

Kapura and Gates report in an article "Sulfonated Polymers as Alkylation Catalysts", Industrial Engineering Chemistry Product Research Development, Vol. 12, No. 1, pp. 62–66 (1973), on tests of several sulfonated polymers for activity as alkylation catalysts. All of the experiments by these authors were carried out in vapor phase and they found that the catalysts rapidly desulfonated and formed coke. No alkylation products were obtained from a feed of isobutane and propylene in a mole ration of about 5/1 with a sulfonated fluorocarbon vinyl ether polymer at 260° C. In aromatic alkylation the other sulfonated polymers lost acidity; the acidity loss could not be measured for the fluorocarbon polymer because the catalyst partially fused. The authors concluded that "none of the sulfonated polymers will be a practically useful catalyst at temperatures greater than about 150° C.". Regardless of Kapura et al's speculation, without data about liquid phase aromatic alkylation with sulfonated polymers generally, their vapor phase data, even at the lower temperature, indicates the opposite: None of the sulfonated polymers tried by Kapura et al would be expected to be effective as commercial alkylation catalysts. The present invention is a liquid phase aromatic alkylation process with fluorocarbon polymer sulfonic acid catalyst and is based upon the finding that substantially higher selectivities are obtained than reported by Kapura and Gates.

SUMMARY OF THE INSTANT INVENTION

The instant invention relates to an aromatic alkylation liquid phase process which is carried out in the presence of a solid fluorocarbon sulfonic acid catalyst. More particularly, the process of the instant invention relates to the alkylation of an aromatic compound with an olefin and comprises the step of contacting said compound and said olefin at reaction conditions in the presence of a polyfluorosulfonic acid catalyst. Preferably, the aromatic compound is a hydrocarbon, e.g. benzene and the olefin is a $C_2$ to $C_{20}$ olefinic material, preferably the lower molecular weight olefins, ethylene and propylene, and most preferably ethylene.

In one aspect of the invention, the hydrocarbon is benzene and the olefinic reactant is selected from the group consisting of $C_2$ to $C_{20}$ olefins, especially alpha olefins. For example, when the desired reaction product is ethylbenzene, the olefin is ethylene, while when the desired reaction product is isopropylbenzene, propylene is used as the olefin. One commercially desirable reaction product is dodecylbenzene which is useful in the preparation of synthetic detergents. This alkylated product is prepared by the reaction of dodecene and benzene.

In general, the olefins which are useful as alkylating agents in the process of the instant invention include ethylene, propylene, 1-butene, 2-butene, 2-methyl-1-butene, 1-hexene, 2-methyl-1-hexene, 1-heptene, 3-heptene, 4-octene, 2-decene, 3-methyl-1-decene, 4-ethyl-1-decene, dodecene, 2-methylpropene, etc.

Compounds which may be alkylated by means of the process of the instant invention include mono- and polynuclear aromatics, including condensed ring aromatics, having from 6 to 20, preferably 6 to 10 carbon atoms, e.g., benzene, naphthalene, biphenyl, and various alkyl, hydroxy, carboxy, halogen substituted derivatives thereof, providing, however, that at least one site is available which is capable of combination with the alkylating agent, e.g., phenol, methoxybenzene, toluene, or the meta and paraxylene, chlorobenzene, etc.

The polyfluorosulfonic acid catalyst which is used in the process of the instant invention is a fluorocarbon polymer containing pendant sulfonic acid and may be derived from fluorocarbon polymers having mixed chlorine and fluorine substituents, wherein the number of chlorine atoms is not more than about 20% of the total chlorine and fluorine atoms present in said polymer. The perfluorinated derivatives of these materials are particularly useful in the process of the instant invention and said perfluorocarbon polymer may have the pendant sulfonic acid attached either directly to the main polymer chain or to perfluorocarbon side chains which are attached to the main polymer chain. Either or both of the main polymer chain and the side chain may contain oxygen atom linkages, such as ether linkages, for example, as in Nafion, TM a perfluorosulfonic acid membrane obtained from E. I. duPont de Nemours and Company (see the description given in Innovation, Vol. 4, No. 3, (1973), pp. 10–13). The perfluorocarbon polymer particularly useful in the present invention may be prepared as disclosed in U.S. Pat. Nos. 3,041,317; 3,282,875; and 3,624,053, hereby incorporated by reference. The most preferred polymers are prepared by copolymerizing a perfluorovinyl ether having the formula:

$$FSO_2CF_2OCF(CF_3)CF_2OCF=CF_2$$

and tetrafluoroethylene followed by conversion of the $SO_2F$ groups to sulfonic acid groups. The equivalent weight of the preferred copolymer preferably ranges from 850 to 2500 where the equivalent weight is defined as the average molecular weight per sulfonyl group.

The catalyst may be used in the process of the instant invention in various physical forms, that is it may be fabricated into sheets, hollow tubes, granules having a particle size of from 6 mesh to less than 400 mesh (preferably 10 to 200 mesh), fibers, etc. The catalyst may be used in a supported or unsupported manner, e.g., the catalyst can be coated onto a metal having good heat exchanger properties, as further described below. It is important to note that the catalyst of the instant invention is insoluble in, and inert to deactivation by the various reactant mixtures, at the conditions at which the alkylating process is carried out, thus providing ease of separation and longer catalyst life than the various solid and liquid catalysts used in the prior art, such as sulfonated polystyrene, sulfuric acid, HF, and phosphoric acid supported on kieselguhr.

A critical preparation of the polyfluorosulfonic acid catalyst for use in the alkylation process of the instant invention is necessary. It has been found that the polyfluorosulfonic acid, that has not been treated as described below, is much less active in catalyzing the alkylation process. However, an active catalyst is conveniently obtained by means of a process which comprises the sequential steps of (1) contacting polyfluorosulfonic acid with a strong acid (pka less than zero) at elevated temperatures, e.g., 70% nitric acid at a temperature of about 110° C., (2) contacting said acid treated polyfluorosulfonic acid of step (1) with distilled water for a time sufficient to remove soluble, residual acid, and (3) drying the polyfluorosulfonic acid of step (2) by contacting with a dry, inert gas, for example, nitrogen containing less than 10 ppm water at a temperature of at least 120°, more preferably from 140° to 180° C. for a time of at least 2 hours, more preferably for from about 4 to about 6 hours. Alternatively, step (3) can be carried out by drying the polyfluorosulfonic acid of step (2) by heating under vacuum at temperatures of from 140° to 180° C. for a period of at least two hours.

The catalyst may be cleaned after use in the same manner, that is, it has been found that when running the process of the instant invention at high temperatures the catalyst tends to darken and lose some activity. It is noted that although the catalyst appears blackened it is still active for carrying out the alkylation process. However, the catalyst may be conveniently cleaned by means of the above-described technique. The catalyst may be cleaned batchwise or, alternatively, the catalyst may be continuously separated from the various reactant and reactant products and cleaned prior to recycling to the reaction. The preferred procedure for reactivating such catalyst is more fully described and claimed in my copending application, Ser. No. 904,503, filed May 10, 1978 now U.S. Pat. No. 4,188,308, issued on Feb. 12, 1980.

In the process of the instant invention, the aromatic compound which is to be alkylated is contacted with an olefin in the presence of the above-described catalysts. The temperature and pressures are maintained to maximize the formation of the desired product, usually the monoalkylate. The ratios of olefin and aromatic compound are varied to ensure that only a very small amount of polymerization product is obtained, for example, the ratio of the aromatic compound to the olefin may be from about 1.5:1 to about 10:1 and higher and is preferably held at a level of from 2 to 1, more preferably from 10 to 1 to ensure that the olefin will not self react to form a polymeric product or react further with the monoalkylation product. The adjustment of temperature and pressures to obtain the desired product would be also obvious to the skilled artisan. For example, temperatures of from 0° C. to 200° C. and pressures of from 0 psig to 1000 psig may be conveniently used although the specific operating pressures will relate to the specific organic compounds and olefins which are to be used. In general, the pressure is adjusted so as to keep the aromatic compound in the liquid phase at the catalyst operating temperature. The temperature is chosen so as to provide a convenient conversion rate while minimizing tar formation on the catalyst. The olefin and aromatic compound feed rates are adjusted so at to provide substantially complete conversion in the time of passage through the catalyst zone, as evidenced by a lack of olefin in the reactor effluent. Feed rates can also be defined in terms of the weight hourly space velocity (WHSV), i.e., the weight per hour of total feed divided by the weight of catalyst employed. The WHSV may vary from about 0.5 to about 20, preferably about 1.5 to 10.

The presence of moisture and other impurities should be avoided in carrying out the process of alkylation. Basic materials should also be excluded from contact with the reactants and the catalyst during the alkylation reaction. For example, amines, inorganic bases, e.g., NaOH, sulfur compounds, for example $CH_3SH$, $CH_3—S—S—CH_3$ should be carefully excluded. The skilled artisan will especially appreciate that no more than 0.05 wt. % water, preferably no more than 0.01 wt. % water, should be present in the reactant feed streams.

In the specific examples given above, that is the alkylation of benzene to form plastic and surfactant precursors, the following reaction parameters may be conveniently used: benzene may be contacted with ethylene at a temperature of from 50° to 190° C. and a pressure of from 0 psig to 150 psig. The ratio of benzene to ethylene is kept at a level of from 10 to 3 to maximize the formation of the monoalkylated product. When propylene is substituted for ethylene, the temperature and pressures may vary from 30° to 190° C. and 0 to 100 psig, respectively. The ratio of benzene to propylene will be maintained at 10 to 3. Since propylene is more reactive as an alkylating agent than ethylene, the ratio of benzene to propylene should be kept higher. At the higher temperatures, it is preferred to use the higher ratios of aromatic compounds to the alkylating olefin in order to minimize side reactions and polyalkylation.

It will thus be apparent from the above specific example that it is very desirable to maximize the formation of the monoalkylate product. In one much preferred mode of operating the process of the instant invention, which is described in the attached FIGURE, a mixture of the organic compound which is to be alkylated and various alkylated derivatives thereof are refluxed in zone 10. An overhead product comprising the organic compound, said product being substantially free of the alkylated derivatives is separated from the mixture and led through conduit 11 into zone 12 wherein it is condensed. The alkylating olefin is brought into zone 12 through line 13 and contacted therein which the condensed overhead product in the presence of the catalyst of the instant invention. Conditions are maintained in zone 12 sufficient to convert at least a portion of the organic compound present in said condensed overhead product to the monoalkyl derivative thereof. The monoalkyl derivative may be returned via conduit 18 along with the unconverted organic compound to zone 10. The unreacted olefin is passed through conduit 14 into zone 15 wherein it may be recovered and recycled via conduit 19 to zone 12. In one preferred embodiment of the process of the instant invention, fresh organic compound is continuously added through line 16 to zone 10 while a fraction containing a substantially high amount of the alkylated derivatives of said organic compound is withdrawn through conduit 17. When operating in this manner, the following advantages are obtained. An organic compound essentially free of its higher boiling alkylated derivatives is continuously contacted with the olefinic stream in zone 12. Thus, the selectivity to the monoalkylated product is increased. Furthermore, heat of the alkylation reaction is converted to heat of vaporization in the catalyst zone 10, thereby maintaining microscopic temperature control at the catalyst sites and obtaining heating economy.

It is noted that the skilled artisan may make various variations on this preferred mode of operation, all of which are within the spirit of the instant invention. For example, the first reactant may be condensed in the same zone in which the solid acid catalyst is contained or may be condensed in a tower at a point located above the solid acid catalyst and fed by gravity to the catalyst zone. The reaction which takes place in the presence of a catalyst is liquid phase with respect to the aromatic compound and thus the reaction can be three phase, namely, a solid catalyst phase, a liquid aromatic compound phase and a gaseous olefin phase. It is preferred to operate the catalyst zone near the boiling point of the combined liquid phase at the selected pressure. With benzene and the preferred olefin, ethylene and propylene, as reactants, ideal design operating conditions are, for example, 200 psi and 200° C., i.e., near the vapor pressure of benzene at this temperature.

Other reactor designs to carry out the process of the instant invention will be well known to the skilled artisan. Some specific reactor designs are described hereinbelow.

SPECIFIC EMBODIMENTS

Four reactor configurations were utilized for the alkylation reactions:

Reactor #1

A stainless steel tube (304 SS, $35'' \times \frac{1}{4}''$ O.D. $\times 0.200''$ I.D.) packed tightly with Nafion TM fiber (1200 equivalent weight (E.W.); 18.8 g, <0.001 diameter) and fitted with tube fittings on each end.

Reactor #2

A stainless steel tube (304 SS, $34'' \times \frac{1}{4}''$ O.D. $\times 0.200''$ I.D.) surrounding a tightly-packed bundle of parallel tubular Nafion TM membranes, 1200 E.W., each 0.024'' I.D. $\times 0.036''$ O.D.) cut flush with the ends of the stainless steel jacket tube. The total weight of the membrane material was 9.32 g.

Reactor #3

A FEP-Teflon TM tube, ($112'' \times \frac{1}{4}''$ O.D. $\times 0.186''$ I.D.) filled with granular Nafion TM resin (57-60 g, 1200 E.W., screened 20/40 mesh) and fitted with glass wool plugs and reducing unions on each end.

The above reactors were mounted in a forced-fan oven controlled to ±0.5° C. Check valves were placed on the exit of the reactor to provide back pressure in the system. Olefin and benzene were mixed (as two phases) in a "cross" at the entrance of the reactor; the fourth arm of the cross was connected to a pressure gauge.

Olefin flow was monitored by a small "rotometer" calibrated for each gas used over a range of pressures encompassing the actual pressures used. Benzene flow was provided either from a calibrated syringe pump or from a metering pump. Samples were collected from the reactor exit into $18 \times 150$ mm test tubes and quickly sealed before analysis.

Reactor #4

"Recycling Reactor" (the preferred mode described above)

A boiling flask (500 ml, with side arm) was fitted (in ascending order) with (1) a vacuum-jacketed fractionating column (2 cm I.D. $\times 29$ cm) filled with stainless steel helice packing, (2) a short connecting tube with a side arm for introduction of gaseous olefin, (3) a reflux condenser with Nafion TM fiber packed into the inner tube of the condenser and vacuum applied to the annular jacket, (4) a water-cooled reflux condenser, (5) a bubbler filled with fluorocarbon oil, for monitoring exit gas, (6) a drying tube connecting to the atmosphere.

To initiate reaction, benzene was refluxed through the system to the upper condenser; then olefin was introduced through the gas inlet. Samples were periodically withdrawn from the pot with a syringe and analyzed by gas chromatography.

Nafion TM perfluorosulfonic acid resin was obtained from duPont, Wilmington, Del. Weights of resin are those before any processing, i.e. equilibrated with atmospheric humidity. After packing the resin into the reactor, it was prepared for use by successive passage of (1) 70% nitric acid at 110° C., (2) distilled water, and (3) dry nitrogen at 140°-160° for 4-6 hours. The last step is critical to the activity of the resin as a catalyst in removing the water of hydration.

Benzene was dried by distillation through a helice packed column from phosphorus pentoxide, prior to use.

at which gas was observed in the outlet, at which point conversion dropped sharply (Table II).

TABLE I

Reaction of Ethylene with Benzene in the Presence of Nafion ™
Reactor #1
Benzene Flow 0.28 ml/min

| Sample | T (°C.) | Ethylene Flow (ml/min) | P (psig) | Ethylene mmoles/min | Ethylbenzene (% wt/vol) | Diethylbenzene(s) (% wt/vol) | Triethylbenzenes (% st/vol) |
|---|---|---|---|---|---|---|---|
| 2 | 41 | 2 | 33 | 0.6 | 4.5 | 0.27 | — |
| 4 | 52 | 2 | 35 | 0.7 | 2.9 | — | — |
| 6 | 62 | 2 | 35 | 0.7 | 4.0 | 0.2 | — |
| 8 | 73 | 2 | 32 | 0.6 | 15.4 | 2.14 | 0.2 |
| 10 | 83 | 4 | 35 | 1.0 | 18.1 | 3.4 | 0.6 |
| 12 | 83 | 8 | 35 | 1.9 | 21.9 | 4.5 | 1.6 |
| 14 | 82 | 8 | 35 | 1.9 | 17.1 | 3.0 | 0.5 |
| 16 | 92 | 8 | 35 | 1.9 | 19.1 | 6.1 | 2.0 |
| 18 | 102 | 8 | 38 | 2.0 | 13.1 | 4.2 | 1.6 |
| 20 | 110 | 8 | 35 | 1.9 | 13.2 | 3.4 | 1.1 |
| 22 | 120 | 8 | 37 | 2.0 | 14.5 | 4.4 | 1.4 |
| 24 | 132 | 8 | 35 | 1.9 | 18.1 | 10.2 | 3.7 |

8 had all liquid in effluent; otherwise excess ethylene flow in all cases.

TABLE II

Conditions as in Table I, except Benzene Flow 0.17 ml/min, T = 94.5° C.

| Sample | Ethylene Flow (ml/min) | P psig | Ethylene mmoles/min | Ethylbenzene (% wt/vol) | Diethylbenzene (% wt/vol) | Triethylbenzene (% wt/vol) | Comments |
|---|---|---|---|---|---|---|---|
| 4 | 0.5 | 32 | 0.15 | 6.1 | 0.3 | — | All liquid |
| 6 | 1.0 | 33 | 0.3 | 12.5 | 1.4 | 0.27 | All liquid |
| 8 | 2 | 35–37 | 0.6 | 21.3 | 3.7 | 0.8 | All liquid |
| 10 | 4 | 32 | 1.0 | 52 | 10.6 | 1.6 | All liquid |
| 12 | 12 | 32 | 2.4 | 13.1 | 2.6 | 0.7 | Mostly gas |
| 14 | 25 | 32 | 4.4 | 6.8 | 1.0 | — | Mostly gas |

EXAMPLE 1

Reaction of Ethylene with Benzene

Concomitant flow of a two-phase mixture of benzene and ethylene through a tubular reactor packed with Nafion ™ polymer (tube bundle, fiber, or granular form) led to efficient conversion of the ethylene to ethyl benzene and small amounts of polyethylbenzenes. The effect of increasing both temperature and ethylene flow rate was investigated; the ethylene flow was in general kept higher than the point at which gas was observed in the effluent from the reactor (unreacted ethylene). This led to relatively poor conversion (Table I), due both to the unreacted ethylene and to "channeling" of gas flow through the reactor. A broad temperature optimum is seen at 80°–90°.

Ethylene flow was increased at constant temperature and benzene flow. Conversion increased until the point Results were essentially the same using a longer tube filled with granular resin (Reactor #3); the transparent FEP Teflon ™ tube enabled visual observation of the ethylene absorption and any channeling. Contact of ethylene with dry Nafion ™ resin with or without the presence of benzene produced an immediate yellow-green coloration of the resin. Both temperature and ethylene flow were increased in this experiment, maintaining the ethylene flow below the point at which significant amounts of gas appeared in the effluent. A broad temperature maximum was again observed, in this case about 95°–105°; above this temperature conversion was essentially constant. Higher temperature did lead to considerable discoloration of the resin; however, activity for ethyl benzene production continued even after the resin had become entirely black (Table III). With different apparatus higher temperature and pressures could have been used.

Preparative runs were made with both of the above reactors to test catalyst life and confirm the product identifications.

TABLE III

Reaction of Benzene with Ethylene
Reactor #3: 9' Tube, Granular Nafion Resin (20/40 Mesh)

| Sample | T (°C.) | Ethylene Flow (ml/min) | P (psig) | Ethylene mmoles/min | Benzene ml/min | Ethylbenzene (% wt/vol) | Diethyl-benzene(s) (% wt/vol) | Triethyl-benzenes (% wt/vol) | Comments |
|---|---|---|---|---|---|---|---|---|---|
| 3 | 65 | 4 | 32 | 1.0 | 0.30 | 14.8 | — | — | Some vapor |
| 5 | 76 | 4 | 32 | 1.0 | 0.31 | 12.7 | — | — | All liquid |
| 8 | 76 | 4 | 32 | 1.0 | 0.26 | 13.8 | 2.9 | — | All liquid |
| 9 | 85 | 4 | 32 | 1.0 | 0.49 | 15.5 | 2.8 | — | All liquid |
| 12 | 85 | 10 | 35 | 2.2 | 0.48 | 19.8 | 4.6 | — | All liquid |
| 15 | 85 | 20 | 37 | 3.9 | 0.48 | 17.0 | 4.2 | 1.1 | Mostly gas |
| 17 | 95 | 20 | 35 | 3.8 | 0.48 | 23.3 | 8.2 | 2.6 | All liquid |
| 18 | 95 | 20 | 35 | 3.8 | 0.48 | 24.2 | 9.6 | 2.2 | All liquid |

TABLE III-continued

Reaction of Benzene with Ethylene
Reactor #3: 9' Tube, Granular Nafion Resin (20/40 Mesh)

| Sample | T (°C.) | Ethylene Flow (ml/min) | P (psig) | Ethylene mmoles/min | Benzene ml/min | Ethylbenzene (% wt/vol) | Diethyl-benzene(s) (% wt/vol) | Triethyl-benzenes (% wt/vol) | Comments |
|---|---|---|---|---|---|---|---|---|---|
| 20 | 104 | 20 | 37.5 | 3.9 | 0.48 | 23.0 | 8.9 | 2.8 | All liquid |
| 21 | 104 | 20 | 38 | 4.0 | 0.48 | 26.2 | 7.2 | 5.3 | Some gas |
| 25 | 116 | 20 | 40 | 4.1 | 0.62 | 19.2 | 6.3 | 2.4 | Some gas |
| 26 | 116 | 20 | 40 | 4.1 | 0.62 | 17.8 | 5.9 | 2.1 | Some gas |
| 28 | 125 | 20 | 40 | 4.1 | 0.55 | 16.7 | 6.1 | 2.2 | Mostly gas |
| 30 | 135 | 20 | 33 | 3.6 | 0.62 | 18.7 | 6.6 | 1.7 | Mostly gas |
| 32 | 145 | 20 | 33 | 3.6 | 0.62 | 20.3 | 7.3 | 1.0 | Reactor black |

EXAMPLE 2

Ethylbenzene from Ethylene and Benzene using Reactor #3

The reactor was cycled in the usual manner with final drying at 185° for several hours. It was cooled to 95°, fitted with an exit check valve, and filled with benzene. When the reactor was nearly filled, ethylene was added into the inlet flow. Samples of the effluent were analyzed for ethyl benzene content (Table IV). Samples 2-8 (400 ml) were pooled and distilled through a vacuum-jacketed column (2.0×62 cm) packed with Helipak TM metal packing. Fractions were analyzed by gas chromatography. The infrared spectrum of Sample #11 was identical to authentic ethyl benzene (Table V).

EXAMPLE 3

Reaction of Ethylene with Benzene using Reactor #1

The reactor was cycled in the usual manner, then filled with dry benzene at 94.5°. Ethylene and benzene were introduced at flow rates of 3 ml/min (47–50 psig, 1.05 mmoles/min) and 0.17 ml/min respectively. After steady-state conditions had been established, a total of 348 ml of the effluent was collected and fractionated by careful distillation through the Helipak column above; fractions were analyzed by gas chromatography (Table VI). The infrared spectra of Samples 6 and 8 were identical to those of authentic ethylbenzene and diethylbenzene (mixed isomers) respectively.

TABLE IV

Samples from Demonstration Run, Reaction of Ethylene with Benzene using Reactor #3. Benzene Flow 0.44 ml/min, T = 95° C.

| Sample | Ethylene Flow (ml/min) | P psig | Sample vol/ml | Ethyl-benzene (% wt/vol) | Diethyl-benzene(s) (% wt/vol) |
|---|---|---|---|---|---|
| 1 | 10 | 35 | 25 | 11.1 | 2.4 |
| 2 | 10 | 37 | 20 | 20.0 | 5.4 |
| 3 | 10 | 35 | 22 | 14.7 | 5.3 |
| 4 | 8 | 40 | 270 | 14.3 | 2.6 |
| 5 | 8 | 40 | 25 | 8.4 | 0.7 |
| 6 | 8 | 40 | 25 | 8.6 | 0.8 |
| 7 | 8 | 40 | 25 | 7.8 | 0.4 |
| 8 | 8 | 40 | 25 | Not observed | |

TABLE V

Distillate Fractions from the Preparative Run of Table IV.
P = 730-733 mm, % Reported is Integration Ratio of Observed Peaks up to 240° on Gas Chromatographic Analysis of Neat Samples (0.15 μl)

| # | T Head (°C.) | T Pot °C. | Vol. or Wt. | Benzene % | Ethylbenzene % | Diethylbenzene % | Triethyl and Higher Benzene (%) |
|---|---|---|---|---|---|---|---|
| 1 | 78.5 | 84–85 | 35 ml | 100 | — | — | — |
| 2 | 78.5 | 85–86 | 66 ml | 100 | — | — | — |
| 3 | 78.5–78.8 | 86–87 | 85 ml | 100 | — | — | — |
| 4 | 78.5 | 87–97 | 85 ml | 100 | — | — | — |
| 5 | 78.8 | 97–137 | 55 ml | 100 | — | — | — |
| 6 | 78–126 | 137–141 | 6.0 g | 96 | 4.4 | — | — |
| 7 | 126–133 | 141 | 0.6 g | 27 | 73 | — | — |
| 8 | 133–134 | 141 | 0.2 g | 9.8 | 90 | — | — |
| 9 | 134 | 141 | 0.9 g | 15.7 | 84 | — | — |
| 10 | 134.5 | 141 | 0.4 g | 12.3 | 88 | — | — |
| 11 | 135 | 144–178 | 40.4 g | 0 | 100 | — | — |
| 12 | 135.5 | 178–202 | 6.9 g | 1.4 | 98.6 | — | — |
| 13 | 136–178 | 202–224 | 3.1 g | 0.5 | 41.2 | 58.3 | — |
| 14 | 178–180 | 224–249 | 1.6 g | — | 6.3 | 94.0 | — |
| 15 | Not Obs. | — | 0.7 g | — | 1.5 | 98.4 | — |
| 16 | Pot Residue | | 9.9 g | — | — | 56.5 | 43.5 |

TABLE VI

Distillate Fractions from Reaction of Benzene with Ethylene using Reactor #1.
P = 730 mm, % is Ratio of Integrations for Peaks Obserbed in Gas Chromatographic Analysis up to 240°

| # | T Head °C. | T Pot °C. | Sample wt (g) | Benzene (%) | Ethylbenzene (%) | Diethylbenzene (%) | Triethyl and Higher (%) |
|---|---|---|---|---|---|---|---|
| 1 | 78.8 | 90 | 76.9 | — | — | — | — |
| 2 | 78.8 | — | 85.0 | 100 | — | — | — |
| 3 | 78.8 | 140 | 25.4 | 100 | — | — | — |
| 4 | 79–129 | 140–141 | 5.6 | 90.1 | 9.9 | — | — |

TABLE VI-continued

Distillate Fractions from Reaction of Benzene with Ethylene using Reactor #1.
P = 730 mm, % is Ratio of Integrations for Peaks Obserbed in Gas Chromatographic Analysis up to 240°

| # | T Head °C. | T Pot °C. | Sample wt (g) | Benzene (%) | Ethylbenzene (%) | Diethylbenzene (%) | Triethyl and Higher (%) |
|---|---|---|---|---|---|---|---|
| 5 | 129–134 | 141–141.5 | 1.9 | 11.6 | 88.3 | — | — |
| 6 | 134 | — | 68.6 | — | 100 | — | — |
| 7 | 135–179 | — | 4.7 | 0.7 | 45.0 | 54.3 | — |
| 8 | 180–181 | to 305 | 13.8 | 0.2 | 0.75 | 99.2 | — |
| 9 | Pot Residue | — | 10.6 | — | 0.3 | 26.3 | (41.8 + 31.6) |

EXAMPLE 4

Monoalkylation of Benzene by Ethylene, Recycling Reactor Design (Reactor #4)

A bundle of Nafion TM "fibers" (<0.001" diam, 1200 E.W., 14.9 g) was pulled into the inner tube of a reflux condenser (1 cm I.D.×40 cm). The condenser was plugged at the bottom, filled with 70% nitric acid, and heated by circulating steam through the condenser jacket. The fiber bundle was then washed with distilled water and dried at 160° with a slow flow of dry nitrogen. The reactor was quickly assembled and 250 ml of dry benzene was placed in the pot. The outer jacket of the catalyst tube was evacuated to minimize heat loss. Reflux was established through the catalyst section; the reflux rate at the bottom of the catalyst tube was approximately 80 drops/min. Ethylene (0.15–0.26 mmoles/min) was introduced into the system; gas flow was observed in the exit bubbler. Samples of approximately 2 ml were periodically removed by syringe from the pot (Table VII).

The residual pot contents (170.5 g) were fractionated by distillation through a 50 cm×1 cm I.D. vacuum-jacketed vigreaux column equipped with a reflux ratio head; the resultant fractions were analyzed by gas chromatography (Table VIII). The conversion of ethylene recovered as ethylbenzene was about 17%.

TABLE VII

Samples from Reaction of Ethylene with Benzene in Recycling Reactor (Reactor #4)
T reaction = 78–79; Ethylene Flow 0.15–0.26 mmoles/min; Reflux Rate 80 Drops/min

| Sample | t (hrs) | Ethylbenzene (% w/v) | Diethylbenzene(s) (% wt/vol) |
|---|---|---|---|
| 1 | 0 | 0 | — |
| 2 | 1.5 | 0.03 | — |
| 3 | 9.0 | 0.58 | — |
| 4 | 22.5 | 1.50 | — |
| 5 | 29 | 2.26;2.32 | — |
| 6 | 32.5 | 2.86 | — |
| 7 | 43.5 | 3.91 | — |
| 8 | 50 | 4.64 | — |
| 9 | 68 | 6.95 | — |
| 10 | 74 | 7.82 | — |
| 11 | 90.5 | 10.9 | — |
| 12 | 102 | 11.6 | — |
| 13 | 115.5 | 13.2 | — |
| 14 | 126 | 14.5 | — |
| 15 | 144 | 18.1 | Trace |
| 16 | 169 | 24.1 | 0.37 |
| 17 | 236 | 30.0 | 0.45 |

TABLE VIII

Distillate Fractions from the Reaction of Table VII,
P = mm, % is Ratio of Integration on all Peaks Observed on Gas Chromatography of Neat Samples up to 240°

| Fraction | Wt (g) | T (°C.) | T pot | Benzene (%) | Ethylbenzene (%) | Diethylbenzene (%) | Triethylbenzene (%) |
|---|---|---|---|---|---|---|---|
| 1 | 73.0 | 79.2–80 | 89–110 | ~100 | Trace | — | — |
| 2 | 14.7 | 80–132 | 110–136 | 87 | 13 | — | — |
| 3 | 42.4 | 133–135.5 | 136–138 | Trace | 100 | — | — |
| 4 | 20.0 | 135.5 | 136.5–139 | — | 100 | — | — |
| Pot Residue | 3.4 | — | — | — | 58 | 38 | 4 |

153.5 = 90.0% recovery $$\text{Total Ethylbenzene} = \frac{(0.13)(14.7\ g) + 42.4\ g + 20.02\ g + (.58)(3.4)}{170.5\ g}$$

= 39% w/w or 34% w/v

EXAMPLE 5

Reaction of Propylene with Benzene

Compared to ethylene, propylene reacted with benzene in the presence of Nafion TM at much higher rates at lower temperatures. Indeed, immersion of the reactor in a water bath was necessary to maintain temperature control. Using Reactor #3, propylene flow was increased at several constant temperatures (Table IX). A preparative sample was taken after Sample 22 at conditions of: T=71°; benzene flow 0.56 ml/min; propylene flow 16 ml/min at 37 psig (3.3 mmoles/min) for the first 360 ml of effluent, then 20 ml/min at 37 psig (2.9 mmoles/min) for 105 ml of effluent (465 ml total).

At higher propylene flow rates, a considerable amount of a low-melting, waxy white solid, possibly propylene polymers was observed in the reactor effluent. As can be seen in Table IX, the principal effect of increased propylene flow was an increase in the extent of polyalkylation, with little or no increase in the amount of cumene produced.

The preparative sample (390.8 g) was slowly distilled through the vacuum-jacketed vigreaux column (50×1 cm) used previously; the samples were analyzed further by gas chromatography (Table X).

The reaction of propylene with benzene in the "recycling reactor" (Reactor #4) was also considerably more facile than the corresponding reaction with ethylene.

of 54 hours were fractionated by distillation through the vigreaux column used previously (Table XII). It can readily be seen that the reactor design gives (as in the previous case) essentially monoalkylation as compared to the high proportion of polyalkylation observed in the reaction of propylene with benxene in the usual flow reactor.

TABLE IX

Reaction of Propylene with Benzene Using Reactor #3
Benzene Flow 0.56 ml/min

| # | T (°C.) | Propylene Flow ml/min | P psig | Propylene mmoles/min | Isopropyl-benzene % wt/vol | Diisopropyl-benzene(s) % wt/vol. | Triisopropyl-benzene(s) % wt/vol | Comments |
|---|---|---|---|---|---|---|---|---|
| 10 | 61 | 8 | 36 | 2.0 | 15.6 | 7.6 | 4.2 | All liquid |
| 12 | 61 | 12–13 | 40 | 2.8–3.0 | 17.4 | 12.4 | 11.4 | All liquid |
| 14 | 61 | 27–28 | 40 | 5.0–5.2 | 12.4 | 5.4 | 4.3 | Mostly gas in outlet |
| 18 | 71 | 10 | 32 | 2.4 | 18.4 | 9.4 | 2.4 | All liquid |
| 20 | 71 | 22 | 33 | 3.9 | 20.6 | 15.5 | 11.8 | All liquid |
| 22 | 71 | 37 | 32 | 5.6 | 19.3 | 17.3 | 15.8 | All liquid |
| 25 | 80 | 22 | 33 | 3.9 | 19.1 | 15.3 | 12.2 | All liquid |
| 27 | 80 | 42 | 33 | 6.2 | 18.9 | 17.9 | 19.2 | All liquid |
| 23 | 71 | 16–20 | 37 | 3.3–3.9 | 20.7 | 15.7 | 11.6 | Prep. Sample |

TABLE X

Distillates from Preparative Sample (#23) from Table IX
P = 730 mm

| # | T Head °C. | T Pot °C. | Wt. (g) | Benzene % | Isopropyl Benzene % | Diisopropyl Benzene(s) % | Triisopropyl Benzene(s) % | % Higher Alkylate |
|---|---|---|---|---|---|---|---|---|
| 1 | 80 | to 109 | 85.5 | 100 | — | — | — | — |
| 2 | 80–81 | 109–149 | 62.2 | 100 | — | — | — | — |
| 3 | 81–146 | 149–171 | 9.8 | 99 | 0.4 | — | — | — |
| 4 | 146–151 | | 1.2 | 20 | 80 | — | — | — |
| 5 | 151–154 | 173–210 | 82.0 | — | 99.6 | 0.4 | — | — |
| 6 | 155–204 | 210–218 | 10.3 | — | 84 | 16 | — | — |
| 7 | 204–215 | 219–230 | 48.5 | — | 0.4 | 93 | 7 | — |
| 8 | 215–238 | 230–248 | 39.5 | — | — | 41 | 59 | — |
| 9 | 235–249 | 248–267 | 16.3 | — | — | — | 83 | 17 |
| 10 | 249→ | 267→ | 0.6 | — | — | — | 69 | 31 |
| Pot Residue | | | 7.2 | — | — | — | 17 | 83 |
| | | | 363.1 | = 93% Recovery | | | | |

Total Isopropylbenzene = 91.5 g/370.8 g = 23% w/w, 20% w/v

EXAMPLE 6

Reaction of Propylene with Benzene in "Recycling Reactor" to Produce Isopropylbenzene Nafion fiber (0.006" diam fibers, 18.1 g total) was packed loosely in small bundles in each of the bulbs of an 8-bulb Allihn condenser, then cleaned and dried in the usual manner; the fiber bundles shrank to approximately ⅓ their original volume during the drying process. The recycling reactor was assembled with 100 ml of dry benzene in the pot. Reflux was established through the catalyst reaction, then propylene was introduced at approximately 20 ml/min; no gas was observed in the outlet bubbler. The reactor was allowed to run for 22 hours to a final pot temperature of 118° (Sample #3). The contents of the pot were removed and replaced by 250 ml of fresh dry benzene. Reflux was again established and propylene flow resumed at 0.85 mmoles/min. Samples were removed periodically for analysis (Table XI). The residual pot contents at the end

TABLE XI

Reaction of Propylene with Benzene in the Recycling Reactor (Reactor #4)

Those marked % are ratios of integration on neat samples

| # | Time (hr) | Isopropyl-benzene % wt/vol | Diisopropyl-benzene(s) % wt/vol | Triisopropyl-benzene(s) % wt/vol |
|---|---|---|---|---|
| 3 | (previous run) | 52.1 | 1.7 | — |
| 4 | 0 | 0.46 | — | — |
| 5 | 2.2 | 4.19 | 0.09 | — |
| 6 | 6.7 | 12.5 | 0.35 | 0.08 |
| 7 | 16.5 | 19.9 | 0.58 | 0.07 |
| 8 | 18.5 | 23.8 | 0.84 | 0.16 |
| 9 | 21 | 28.4 | 0.70 | — |
| 10 | 24 | 34.0 | 0.87 | — |
| 12 | 41.5 | 51.3 | 2.98 | — |
| 13 | 47 | 67.2 | 3.4 | 0.7 |
| 14 | 50 | 77% | — | — |
| 15 | 53 | 80.3% | 4.5 | — |
| 16 | (Pot 54 contents) | 76% | 4.8 | — |

0.85 mmoles/min ⇒ 2.75 moles

Total isopropyl groups recovered in product 1.74 moles or 63%

TABLE XII

Distillate Fractions from Distillation of Pot Contents from Reaction in Table XI.
P = 730 mm. % is Ratio of Integrations of Peaks on Gas Chromatographic Analysis to 240°

| # | T Head °C. | T Pot °C. | Wt (g) | Benzene % | Isopropyl-Benzene % | Diisopropyl-Benzene % | Triisopropyl-Benzene % |
|---|---|---|---|---|---|---|---|
| 1 | 80–82.5 | 124–136 | 16.7 | 100 | — | — | — |
| 2 | 82.5–151.5 | 136–154 | 16.5 | 98.3 | 1.7 | — | — |
| 3 | 151.5 | 154.5 | 73.5 | — | 100 | — | — |
| 4 | 151.5 | 155 | 102.5 | — | 100 | — | — |
| 5 | 151.5 | 155–197 | 10.7 | — | 100 | — | — |
| 6 | 152–243 | 197–260 | 14.0 | — | 19. | 79.6 | 1.0 |
| Pot Residue | | | 3.4 | — | 0.67 | 47.7 | 51.6 |
| | | | 237.31 | = 90% recovery | | | |

Benzene 12.5% w/w
Isopropylbenzene 72% w/w
Diisopropylbenzene(s) 5% w/w
Triisopropylbenzene(s) 0.7% w/w

EXAMPLE 7

Production of Mixed Isomers of Linear Dodecylbenzene from Dodecene and Benzene Nafion ™ perfluorosulfonic acid resin (1200 equivalent weight, 0.006" diameter fiber, 3.53 gm.) was formed into a compact bundle and placed inside a 50 ml. round bottom flask equipped with a side-arm outlet, a reflux condenser and a drying tube above the condenser. The assembly was placed in an oven at 150° C. for 4 hours with dry nitrogen flowing slowly through the assembly, then allowed to cool to room temperature while protected from atmospheric moisture. Dodecene-1 (MCB, practical grade) (15.0 g., 0.089 mole) and dry benzene (15.0 g., 0.192 mole) were weighed into the flask and the mixture was heated to reflux for 30 hours. Samples (0.2 ml.) were removed through the side arm for analysis by gas chromatography. The results are shown in Table XIII. The residual pot contents (24.2 g.) were distilled through a 1 × 12 cm. vacuum-jacketed vigreaux column equipped with a reflux ratio take-off head. The results are shown in Table XIV.

TABLE XIII

Gas chromatography analysis of samples from alkylation of benzene with dodecene-1 using submerged Nafion ™ resin catalyst, Example 7. (The figures are integrations or ratio of integrations, all measured directly without use of internal standards for relative F.I.D. response. Column 10' × ⅛", 5% SE 30 silicone on gas chrom Z (100–120 mesh), 130°–230° C. at 10° C./min.)

| Sample | Time (Hr.) | Dodecene | Dodecylbenzene | Didodecylbenzene | Ratio: Diodecyl φ Dodecyl φ | Ratio: Dodecene Dodecene + dodecyl φ + didodecyl φ |
|---|---|---|---|---|---|---|
| 1 | 0 (Cold) | 6.84 | 0 | 0 | 0 | 1 |
| 2 | 0.2 | 14 | 0 | 0 | 0 | 1 |
| 3 | 0.8 | 15 | 0.4 | 0 | 0 | 0.97 |
| 4 | 2.0 | 11.57 | 0.84 | 0 | 0 | 0.93 |
| 5 | 19.8 | 3.72 | 19.4 | 2.3 | 0.12 | 0.15 |
| 6 | 24.0 | 3.99 | 41.0 | 4.0 | 0.097 | 0.08 |
| 7 | 28.5 | 1.40 | 35.4 | 5.3 | 0.15 | 0.03 |

TABLE XIV

Distillate Fractions from Alkylation of Benzene with Dodecene-1 using submerged Nafion ™ resin catalyst, Example 7.

| Fraction No. | T(head) | T(pot) | P(mm.) | Wt. (gm.) | % |
|---|---|---|---|---|---|
| 1 | 47–107° C. | 129–134° C. | 0.6 | 0.05 | 0.3 |
| 2 | 107–131 | 134–164 | 0.5 | 12.8 | 78.3 |
| 3 | 131–179 | 182–239 | 0.8 | 1.6 | 9.8 |
| 4 | 179–219 | 237–312 | 0.9 | 1.3 | 7.9 |
| Pot | | | | 0.6 | 3.7 |

TABLE XIV-continued

Distillate Fractions from Alkylation of Benzene with Dodecene-1 using submerged Nafion ™ resin catalyst, Example 7.

| Fraction No. | T(head) | T(pot) | P(mm.) | Wt. (gm.) | % |
|---|---|---|---|---|---|
| Residue | | | | 16.35 | 100 |

EXAMPLE 8

Dodecylbenzene from Dodecene and Benzene using a modified recycling reactor

Nafion ™ fiber (3.5 g., 0.006" diameter, 1200 equivalent weight, hydrogen form) was loosely packed into a 1 cm. diameter vacuum-jacketed column and dried at 150° C. for 2 hours in a stream of dry nitrogen. The column was fitted onto a 50 ml. round bottom flask equipped with a side arm for sampling. A condenser and drying tube were fitted above the catalyst column. Dodecene-1 (15.0 z.), dry benzene (15.0 g.) and marble boiling chips were added to the flask; reflux was established up to the condenser. Samples (0.2 ml.) were periodically withdrawn via the side arm and analyzed by gas chromatography. The results are shown in Table XV. The residual pot (refluxing flask) contents were distilled through a 1 × 12 cm. vigreaux column equipped with a reflux ratio take off. The results are shown in Table XVI and illustrate that the integrated reactor fractionator is preferred for obtaining monoalkylated products. Although the conversion is somewhat slower by the refluxing of the mixture up to the catalyst, this method provides that only dodecene and benzene are present at the catalyst surface, in a ratio determined by their contributory vapor pressures, resulting in specific conversion to dodecylbenzene with no polyalkylated benzenes produced.

TABLE XV

Gas Chromatography Analysis of Samples from Alkylation of Benzene with Dodecene-1 using catalyst suspended in vapor/condensate, Example 8
(Analysis procedure same as for Table XIII.)

| Sample | Time (Hrs.) | Dodecene | Dodecylbenzene | Didodecylbenzene | Ratio: Didodecyl $\phi$ Dodecyl $\phi$ | Ratio Dodecene Dodecene + dodecyl $\phi$ + didodecyl $\phi$ |
|---|---|---|---|---|---|---|
| 1 | 0 | 11.2 | 0 | 0 | 0 | 1 |
| 2 | 2.0 | 11.4 | 0 | 0 | 0 | 1 |
| 3 | 19.75 | 10.6 | 2.6 | 0 | 0 | 0.80 |
| 4 | 73 | 10.6 | 24.5 | 0 | 0 | 0.30 |
| 5 | 93 | 5.9 | 21.2 | 0 | 0 | 0.22 |
| 6 | 121.5 | 2.7 | 24.1 | 0 | 0 | 0.10 |
| 7 | 139.5 | 2.1 | 32.0 | 0 | 0 | 0.06 |

TABLE XVI

Distillate Fractions from Alkylation of Benzene with Dodecene-1 using catalyst suspended in vapor/condensate, Example 8.

| Fraction No. | $T_{(head)}$ | $T_{(pot)}$ | $P_{(mm.)}$ | Wt. (gm.) | % |
|---|---|---|---|---|---|
| 1 | 53–117° C. | 114–134° C. | 1.2 | 0.5 | 2.6 |
| 2 | 118–120 | 134–137 | 1.1 | 0.1 | 0.5 |
| 3 | 120–131 | 137–215 | 1.1 | 17.9 | 92.3 |
| Pot Residue | | | | 0.9 | 4.6 |
| | | | | 19.4 | 100 |

The foregoing experiments illustrate that with the present process substantially higher selectivities are obtained than reported by Kapura and Gates referred to hereinabove. Thus, these authors reported for conversions of about 5%, a selectivity of the mono-alkylate product to the di- and tri-alkylate products of about 25 to 1; when they increased the conversion to 25%, the selectivity was reduced to only 13% mono-alkylate (page 65 of the article). In comparison, the present process gives, for example, in the results shown in Table IX, No. 14 at a conversion of 28% over half the product as monoalkylate and in Table XI, less than 5% of polyalkylate at a conversion of up to 80%.

What is claimed is:

1. A liquid phase process for the alkylation of an aromatic hydrocarbon with an olefin which comprises contacting said aromatic hydrocarbon and said olefin, at reaction conditions, in the presence of a copolymer of a perfluorovinyl ether and tetrafluoroethylene containing pendant sulfonic acid groups, as catalyst.

2. A liquid phase process for the preparation of ethylbenzene which comprises contacting an ethylene feed stream with a benzene feed stream at a reaction temperature of between about 50° and about 200° C. in the presence of an unsupported catalyst comprising a copolymer of a perfluorovinyl ether and tetrafluoroethylene containing pendant sulfonic acid groups.

3. A process according to claim 2 wherein the mole ratio of said benzene stream to said ethylene stream varies from about 1.5:1 to about 10:1.

4. A process according to claim 2 wherein the weight hourly space velocity, defined as the weight per hour of the reactants divided by the weight of the catalyst employed varies from between about 0.5 to about 20.0 $hr^{-1}$.

5. A liquid phase process for the preparation of ethylbenzene which comprises contacting an ethylene feed stream with a benzene feed stream at a reaction temperature of between about 0° and about 200° C. in the presence of an unsupported catalyst comprising a copolymer of a perfluorovinyl ether and tetrafluoroethylene containing pendant sulfonic acid groups.

6. A process according to claim 5 wherein the mole ratio of said benzene stream to said ethylene stream varies from about 1.5:1 to about 10:1.

7. A process according to claim 5 wherein the weight hourly space velocity, defined as the weight per hour of the reactants divided by the weight of the catalyst employed varies from between about 0.5 to about 20.0 $hr^{-1}$.

* * * * *